US00PP31906P2

(12) United States Plant Patent
Monte-Michielsen

(10) Patent No.: US PP31,906 P2
(45) Date of Patent: Jun. 23, 2020

(54) ***GERANIUM* PLANT NAMED 'TOSTD0342'**

(50) Latin Name: ***Pelargonium* x *hortorum***
Varietal Denomination: TOSTD0342

(71) Applicant: Ball Horticultural Company, West Chicago, IL (US)

(72) Inventor: Fabienne Monte-Michielsen, Brielle (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/501,947

(22) Filed: Jul. 9, 2019

(51) Int. Cl.
*A01H 5/02* (2018.01)
*A01H 6/42* (2018.01)

(52) U.S. Cl.
USPC ..... Plt./330

(58) Field of Classification Search
USPC ..... Plt./324, 325, 330
See application file for complete search history.

*Primary Examiner* — Susan McCormick Ewoldt
(74) *Attorney, Agent, or Firm* — Audrey Charles

(57) ABSTRACT

A new and distinct cultivar of *Geranium* plant named 'TOSTD0342', characterized by its semi-double type, dark red-colored flowers, dark green-colored foliage with zonation, and moderately vigorous, upright-mounded growth habit, is disclosed.

1 Drawing Sheet

Latin name of genus and species of plant claimed: *Pelargonium* x *hortorum.*

Variety denomination: 'TOSTD0342'.

BACKGROUND OF THE INVENTION

The present invention relates to a new and distinct cultivar of *Geranium* plant botanically known as *Pelargonium* x *hortorum* and hereinafter referred to by the cultivar name 'TOSTD0342'.

The new cultivar originated in a controlled breeding program in Hendrik-Ido-Ambacht, the Netherlands during July 2015. The objective of the breeding program was the development of *Geranium* cultivars that flower uniformly and have large flowers, dark green-colored foliage, and a moderately vigorous, upright-mounded growth habit.

The new *Geranium* cultivar is the result of cross-pollination. The female (seed) parent of the new cultivar is CALLIOPE Burgundy 'Cope Burg', not patented, characterized by its semi-double type, dark burgundy-colored flowers, medium green-colored foliage having zonation, and moderately vigorous, upright-mounded growth habit. The male (pollen) parent of the new cultivar is Bernd 'Toscabernd', also sold as Presto Dark Red 'Tospresdared', not patented, characterized by its semi-double type, dark burgundy-colored flowers, dark green-colored foliage having zonation, low vigor and an upright-mounded growth habit. The new cultivar was discovered and selected as a single flowering plant within the progeny of the above stated cross-pollination during August 2016 in a controlled environment in Hendrik-Ido-Ambacht, the Netherlands.

Asexual reproduction of the new cultivar by terminal stem cuttings since August 2016 in Hendrik-Ido-Ambacht, the Netherlands and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'TOSTD0342' as a new and distinct cultivar of *Geranium* plant:

1. Semi-double type, dark red-colored flowers;
2. Dark green-colored foliage with zonation; and
3. Moderately vigorous, upright-mounded growth habit.

Plants of the new cultivar differ from plants of the female parent primarily in having a semi-double type flower, a different shade of red flower color, and darker green-colored foliage. Plants of the new cultivar differ from plants of the male parent primarily in having a different shade of red flower color, and increased growth vigor.

Of the many commercially available *Geranium* cultivars, the most similar in comparison to the new cultivar is Savannah Really Red 'Duesarelre', U.S. Plant Pat. No. 26,984. However, in comparison, plants of the new cultivar differ from plants of 'Duesarelre' in at least the following characteristics:

1. Plants of the new cultivar have a flower color that is lighter red than plants of 'Duesarelre'; and
2. Plants of the new cultivar are shorter and narrower than plants of 'Duesarelre'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'TOSTD0342'. The plants were approximately 4 months old and grown in 4.5-inch pots for approximately 14 weeks in a greenhouse in West Chicago, Ill.

DETAILED BOTANICAL DESCRIPTION

Figure 1:
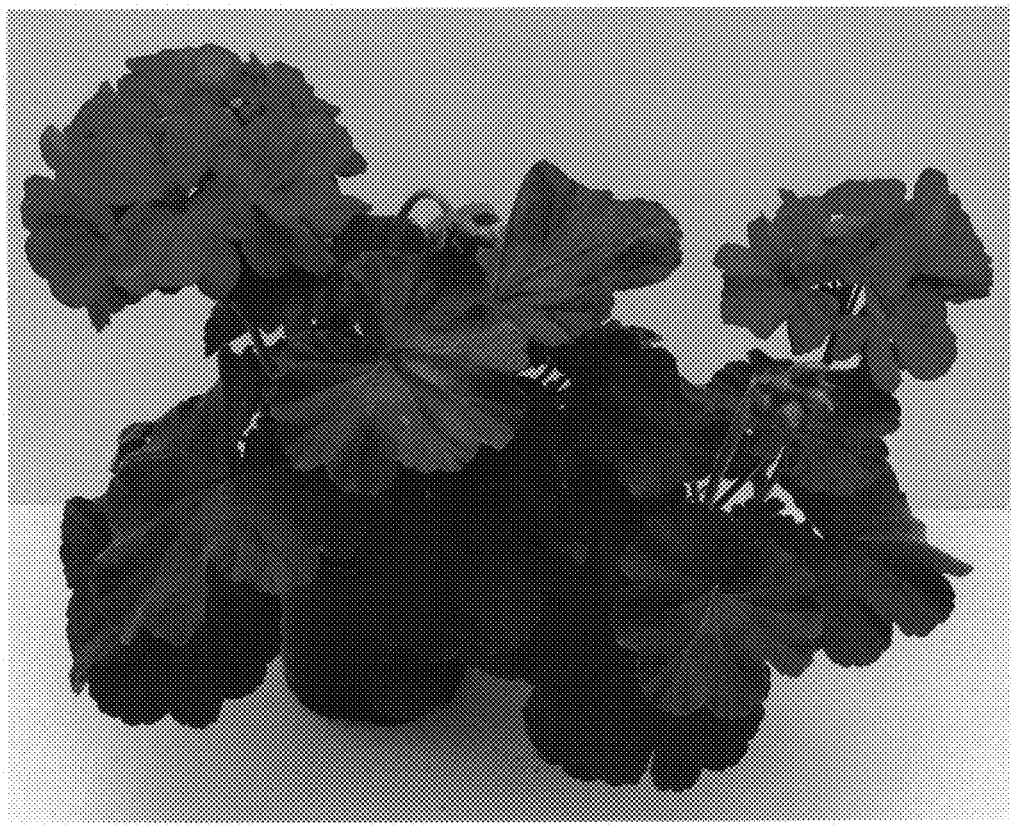
FIG. 1 illustrates a side view of the overall growth and flowering habit of 'TOSTD0342'.
Figure 2:
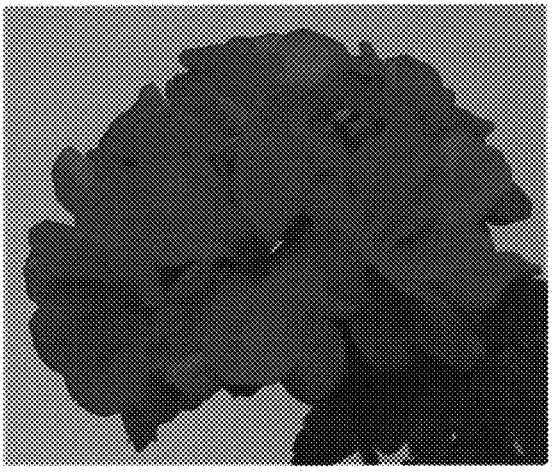
FIG. 2 illustrates a close-up view of an individual umbel of 'TOSTD0342'.
Figure 3:
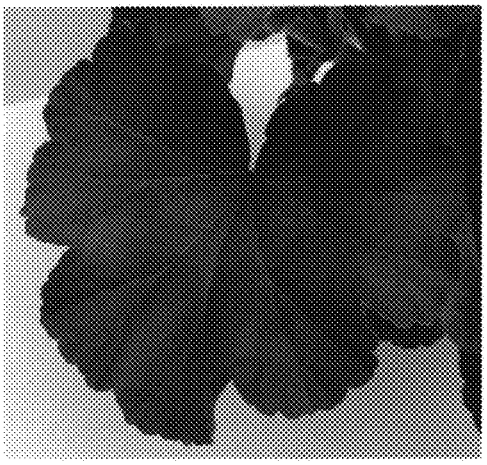
FIG. 3 illustrates a close-up view of an individual leaf of 'TOSTD0342'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in April 2019 under natural light conditions in West Chicago, Ill.

The following descriptions and measurements describe approximately 4-month old plants produced from cuttings from stock plants and grown in a glass-covered greenhouse under conditions comparable to those used in commercial practice. The plants were grown in West Chicago, Ill. in 4.5-inch pots for approximately 14 weeks utilizing a soilless growth medium. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Pelargonium* x *hortorum* 'TOSTD0342'.

Parentage:

*Female parent*.—CALLIOPE Burgundy 'Cope Burg', not patented.

*Male parent*.—Bernd 'Toscabernd', also sold as Presto Dark Red 'Tospresdared', not patented.

Propagation:

*Type cutting*.—Terminal stem.

*Time to initiate roots*.—Approximately 9 to 12 days.

*Time to produce a rooted cutting*.—Approximately 21 to 28 days.

*Root description*.—Fibrous.

*Rooting habit*.—Freely branching.

Plant description:

*Commercial crop time*.—Approximately 8 to 9 weeks from a rooted cutting to finish in a 10 cm pot.

*Growth habit and general appearance*.—Moderately vigorous, upright-mounded.

*Size*.—Height from soil level to top of plant plane: Approximately 22.0 cm. Height from soil level to top of foliage: Approximately 13.5 cm. Width: Approximately 31.5 cm.

*Branching habit*.—Freely basal branching, pinching enhances basal branching. Quantity of main branches per plant: Approximately 2.

*Branch*.—Strength: Strong. Length: Approximately 13.5 cm. Diameter: Approximately 6.5 mm. Length of central internode: Approximately 2.0 cm. Texture: Densely pubescent with a mixture of glandular and nonglandular hairs. Gland color: Colorless, transparent. Color of young and mature stems: 146B.

Foliage description:

*General description*.—Quantity of leaves per branch: Approximately 10. Fragrance: Slight. Form: Simple. Arrangement: Opposite.

*Leaves*.—Aspect: Petiole is at an acute angle to stem, blade is perpendicular to stem. Shape: Reniform. Margin: Bicrenate, palmately lobed, somewhat wavy. Apex: Obtuse. Base: Cordate. Venation pattern: Palmate. Length of mature leaf: Approximately 7.5 cm. Width of mature leaf: Approximately 9.1 cm. Texture of upper and lower surfaces: Densely pubescent with a mixture of glandular and nonglandular hairs. Gland color: Colorless, transparent. Color of upper surface of young and mature foliage: Closest to 137A with a faint overlay of NN137A on zonal area of approximately outer two thirds of leaf and venation of 146B. Color of lower surface of young and mature foliage: Closest to 147B with venation of 146C.

*Petiole*.—Length: Approximately 4.5 cm. Diameter: Approximately 3.0 mm. Texture: Densely pubescent with a mixture of glandular and nonglandular hairs. Gland color: Colorless, transparent. Color: 146B to 146C.

Flowering description:

*Flowering habit*.—'TOSTD0342' is freely flowering under outdoor growing conditions with substantially continuous blooming from spring through autumn and year-round in greenhouse environment.

*Lastingness of individual flower on the plant*.—Approximately 12 to 14 days.

Inflorescence description:

*General description*.—Type: Umbel, semi-spherical. Positioned above foliage. Quantity of fully open umbels per plant: Approximately 2. Quantity of developing umbels per plant: Approximately: 2. Fragrance: Slight. Length or height: Approximately 5.5 cm. Width: Approximately 9.5 cm. Quantity of fully open flowers per inflorescence: Approximately 10.

*Peduncle*.—Strength: Strong. Aspect: Erect. Length: Approximately 14 cm. Diameter: Approximately 4.0 mm. Texture: Densely pubescent with a mixture of glandular and nonglandular hairs. Gland color: Colorless, transparent. Color: 146A to 146B tinted with 187A.

Flower description:

*General description*.—Type: Semi-double.

*Bud*.—Rate of opening: Generally takes 3 to 4 days for bud to progress from first color to fully open flower.

*Bud just before opening*.—Shape: Elliptic. Length: Approximately 1.5 cm. Width: Approximately 8.0 mm. Sepal texture: Densely pubescent with a mixture of glandular and nonglandular hairs. Gland color: Colorless, transparent. Petal texture: Glabrous. Petal color: 53A to 53B.

*Corolla*.—Shape: Round. Diameter: Approximately 4.0 cm. Depth: Approximately 2.0 cm.

*Petals*.—Quantity: Approximately 6 petals and 1 to 2 irregularly-shaped petaloids per flower. Shape: Obovate. Appearance: Iridescent. Margin: Entire. Apex: Obtuse. Base: Attenuate. Length of upper petals: Approximately 3.0 cm. Width of upper petals: Approximately 1.6 cm. Length of lower petals: Approximately 2.6 cm. Width of lower petals: Approximately 2.0 cm. Texture of upper and lower surfaces: Glabrous. Color of upper surface of upper petals when fully open: 53A and 45B, venation of 53A at base. Color of lower surface of upper petals when fully open: Closest to 53B and 45C to 45D, venation of 53A at base. Color of upper surface of lower petals when fully open: 53A and 45B. Color of lower surface of lower petals when fully open: 53B and 45C to 45D.

*Calyx*.—Shape: 5-pointed star. Diameter: Approximately 2.0 cm.

*Sepals*.—Quantity per flower: Approximately 5, fused at base. Shape: Lanceolate. Margin: Entire. Apex: Acuminate. Length of upper sepal: Approximately 1.2 cm. Width of upper sepal: Approximately 4.0 mm. Length of lower sepals: Approximately 1.2 cm. Width of lower sepals: Approximately 2.0 mm. Texture of upper surface: Glabrous. Texture of lower surface: Densely pubescent with a mixture of glandular and nonglandular hairs. Gland color: Colorless, transparent. Color of upper surface: 146B with 187B at base. Color of lower surface: 146B with a heavy overlay of 187A.

*Pedicel*.—Strength: Strong. Aspect: Acute angle to peduncle. Length: Approximately 2.5 cm. Diameter: Approximately 1.5 mm. Texture: Densely pubescent with a mixture of glandular and nonglandular hairs. Gland color: Colorless, transparent. Color: 146B with a heavy overlay of 187A.

*Reproductive organs*.—Androecium: Quantity of mature stamens: Approximately 9 per flower. Anther shape: Oblong. Anther length: Approximately 2.0 mm. Anther color: 71B. Filament length: Approximately 8.0 mm. Filament color: NN155D with an overlay of 67B nearest anther. Pollen amount: Moderate. Pollen color: 32A. Gynoecium: Pistil quantity: 1 per flower. Pistil length: Approximately 9.0 mm. Stigma shape: 5 branched. Stigma length: Approximately 2.0 mm. Stigma color: 185B. Style length: Approximately 2.0 mm. Style color: 185B. Ovary length: Approximately 6.0 mm. Ovary texture: Densely pubescent. Ovary color: 145A.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'TOSTD0342', substantially as herein illustrated and described.

* * * * *